United States Patent [19]

Cohen et al.

[11] Patent Number: 5,185,386

[45] Date of Patent: Feb. 9, 1993

[54] DENTAL COMPOSITION

[75] Inventors: Brett I. Cohen, Nanuet; Barry Musikant, New York, both of N.Y.

[73] Assignee: Essential Dental Systems, Inc., So. Hackensack, N.J.

[21] Appl. No.: 860,279

[22] Filed: Apr. 1, 1992

Related U.S. Application Data

[63] Continuation of Ser. No. 717,886, Jun. 19, 1991, abandoned, which is a continuation-in-part of Ser. No. 669,076, Mar. 14, 1991, abandoned.

[51] Int. Cl.$^5$ .......................... A61K 6/00; C08K 5/34
[52] U.S. Cl. ..................................... 523/105; 523/120; 524/104; 524/507
[58] Field of Search ............................ 106/35; 424/78; 523/105, 120; 524/104, 507

[56] References Cited

U.S. PATENT DOCUMENTS 4,206,102 6/1980 Britain et al. ........................ 524/507

OTHER PUBLICATIONS

J. A. Roberts et al., Journal of Urology, "Bacterial Adherence to Urethral Catheters", vol. 144, Aug. 1990, pp. 264–269.

"Catheters and Kits", p. A–1, Bard Urological Division Catalog, 1990.

*Primary Examiner*—Marianne M. Cintins
*Assistant Examiner*—Rebecca Cook
*Attorney, Agent, or Firm*—Gottlieb, Rackman & Reisman

[57] ABSTRACT

A composition for preventing the build-up of plaque and other debris along the surface of dentures and dental implants is provided. The composition includes a solvent in an amount between about 46 and 98 weight percent, an evaporation promoting compound such as N-methylpyrrolidone in an amount between about 0.5 and 25 weight percent, a polyurethane resin in an amount between about 1 and 35 weight percent and a poly(fluoro) compound such as polytetra-flluoroethylene in an amount between about 0.5 and 20 weight percent.

26 Claims, No Drawings

DENTAL COMPOSITION

This application is a continuation of application Ser. No. 717,886, filed Jun. 6, 1991, now abandoned, which is a continuation-in-part of Ser. No. 669,076 filed Mar. 14, 1991, now abandoned.

BACKGROUND OF THE INVENTION

This invention relates to a dental composition, and more particularly, to a composition which is applied to dentures and other types of artificial teeth as well as to dental implants. The composition is used for preventing the build-up of plaque and other debris.

One of the major problems with dentures and other artificial teeth is that they quickly accumulate plaque and other debris along the surface of the denture material. This is obviously not desirable since wearer comfort is reduced, distasteful odors are produced and denture wearability is decreased.

There are a number of commercial compositions on the marketplace which may be used for cleaning dentures. These compositions include Efferdent, Polident and Dentu-Creme, and are used on or applied to the dentures when outside the mouth of the wearer. However, such compositions are less than satisfactory. These composition are not totally efficient and may not fully clean the dentures because of the excessive build-up of plaque and debris. In some cases, a toothbrush or other manual cleaner may be needed.

One of the recurring problems with dental implants is also the accumulation of plaque, particularly at the gingival level. To be removed, the dentist must take a Teflon coated instrument and scrape the material away. This results in scratches along the surface of the implant and also promotes further plaque accumulation in the future.

In the medical field, there are chemical formulations that have been used to form a coating along the surface of medical devices such as catheters. This type of coating provides a dry lubricated surface which reduces friction and drag. As a result, performance of these devices is enhanced. These chemical formulations have in the past comprised a ketone based composition that includes N-methylpyrrolidinone, a polyurethane resin and polytetrafluor-ethylene (Teflon).

In view of the previous success of this composition in forming a coating surface on medical equipment which exhibits reduced friction and drag, it would be desirable to determine whether the composition has application in the dental field, specifically as a coating for a denture material or dental implant.

SUMMARY

Generally speaking, in accordance with the invention, a composition for preventing the build-up of plaque and other debris on artificial teeth and dental implants is provided. The composition includes a solvent in an amount between about 46 and 98 weight percent, an evaporation promoting compound such as N-methyl-pyrrolidinone in an amount between about 0.5 and 25 weight percent, a polyurethane resin in an amount between about 1 and 35 weight percent and a poly(fluoro) compound such as polytetra-fluorethylene (Teflon) in an amount between about 0.5 and 20 weight percent.

The composition of the invention is prepared by mixing the N-methylpyrrolidinone, the polyurethane resin and the polytetra-fluorethylene in the solvent until the chemicals dissolve and a homogeneous material is produced.

For application to dentures, the composition of the invention is typically sprayed on all external surfaces of the dentures and then allowed to dry.

For application to a dental implant, the composition is applied by dipping the implant in the composition (a solution) and then allowing the implant to dry. Alternatively, the composition may be applied to the implant by painting.

Accordingly, it is an object of this invention to provide an improved composition for preventing the build-up of plaque and other debris on artificial teeth and dental implants.

Another object of the invention is to provide an improved dental composition for preventing the buildup of plaque and other debris which may be easily applied by spraying or dipping.

A further object of the invention is to provide a dental composition for preventing the build-up of plaque and other debris by forming a coating along the surface of the dental material for reducing friction and drag therealong.

Still another object of the invention is to provide a dental composition which increases retention of dentures in the mouth of the wearer.

Yet a further object of the invention is to provide an improved composition which reduces odors in the mouth.

Still other objects and advantages of the invention will in part be obvious and will in part be apparent from the following description.

The invention accordingly comprises the several steps and the relation of one or more of the steps with respect to each of the others, and the composition or compositions having the features, properties, and relation of constituents which are exemplified in the following detailed disclosure, and the scope of the invention will be indicated in the claims.

DETAILED DESCRIPTION OF THE PREFERRED EMBODIMENT

The composition of the invention includes a solvent in an amount between about 46 and 98 weight percent. The solvent may be chosen from water, alcohols and ketones.

Suitable alcohols include ethanol, methanol, isopropyl alcohol, 3-pentanol, 2-pentanol, 1-pentanol, 1-hexanol, 2-hexanol, 3-hexanol and isobutyl alcohol. The preferred alcohol is ethanol in an amount between about 50 and 97 weight percent.

Suitable ketones include methylethyl ketone, acetone, allylacetone, isopropyl acetone, methylpropyl ketone, 3-pentanone, 3-hexanone and 2-hexanone. The preferred ketone is methylethyl ketone in an amount between about 50–97 weight percent.

The preferred amount of water (if chosen as the solvent) in the inventive denture composition is in an amount between about 50 and 97 weight percent.

In order to have a rapid mechanism for drying, the composition of the invention includes an evaporation promoting compound in an amount between about 0.5 and 25 weight percent. The evaporation promoting compound is chosen from a pyrrolidone based or an ether based material. The preferred compound is a pyrrolidone based material chosen from N-methylpyrrolidinone (NMP), 2-pyrrolidone, 2-pyrrolidoneacetamide, 1-ethyl-2-pyrolidinone and 5-methyl-2-pyrrolidinone. N-methylpyrrolidinone is the preferred pyrrolidone material and may be present in the composition in an amount between about 1 and 20 weight percent.

If an ether based material is instead chosen as the evaporation promoting compound of the inventive composition, it could be chosen from diethylether, isopropylether and pentylether.

As stated above, the purpose of including an evaporation promoting compound such as N-methylpyrrolidinone in the composition is to promote rapid drying of the composition when applied to either a denture material or a dental implant. This is achieved by accelerating evaporation at room temperature, thereby leaving a coating on the denture material or dental implant.

The inventive composition also includes a polyurethane resin in an amount between about 1 and 35 weight percent. If the solvent chosen is either water or an alcohol, a water-based aliphatic polyurethane resin is chosen and is preferably present in an amount between about 2 and 25 weight percent. If instead a ketone is used as a solvent, a non-water-based aromatic polyurethane resin is used and is preferably present in an amount between about 2 and 25 weight percent.

Suitable water-based aliphatic polyurethane resins include adducts of 1,6-hexane diisocyanate (HDI) and isophorone diisocynate (IPDI), each with any of the following polyols: polyethylene oxide (PEO), polypropylene oxide (PPO), polyiosbutylene (PIB) and polytetramethylene oxide (PTMO). Therefore, a water-based polyurethane resin could be HDI/PPO, IPDI/PTMO or any other combination with an alphatic diisocyanate and a polyol group.

Suitable non-water based aromatic polyurethane resins include adducts of 2,4 toluene diisocyanate (2,4 TDI), 2,6 toluene diisocyanate (2,6 TDI), methylene bis (p-phenylisocyanate) (MDI), and 1,5-naphathalene diisocyanate (NDI), each with either of the following polyols: polyethylene oxide (PEO), polypropylene oxide (PPO), polyiosbutylene (PIB) and polytetramethylene oxide (PTMO). Therefore, a non-water based polyurethane resin could be 2,4 TDI/PPO, 2,4 TDI/PTMO, MDI/PPO, MDI/PEO, NDI/PEO or any other combination with an aromatic diisocyanate and a polyol group.

In addition, the polyurethane resin could also have a chain extender group such as ethylene glycol (EG), hexanediol (HD), 4,4 methylene bis (2-chloroaniline) (MOCA) and ethylene diamine (ED). Therefore, the polurethane resin can be HDI/ED/PPO and IPDI/EG/PTMO (water based polyurethanes), or 2,4 TDI/ED/PPO, 2,4 TDI/MOCA/PTMO, MDI/EG/PPO: MDI/ED/PEO and NDI/ED/PEO (non-water based polyurethanes).

The purpose of including a polyurethane resin in the inventive composition is to provide a hard, resistant coating (a chemical matrix) in order to "lock in" the Teflon on the applied surface of the denture or dental implant. It also increases wearability of the material to which the inventive composition is applied.

The inventive dental composition further includes a poly(fluoro) compound such as a fluorinated hydrocarbon in an amount between about 0.5 and 20 weight. The preferred fluorinated hydrocarbon is polytetrafluoroethylene (Teflon) in an amount between about 0.5 and 15 weight percent. The purpose of including Teflon in the composition is to prevent the build-up of plaque and other debris and dirt on the surfaces of the denture or dental implant, and also to reduce drag and resistance under normal wear.

Instead of using polytetra-fluorethylene in the composition, the composition may include as a fluorinated hydrocarbon polychlorotrifluoroethylene, polyhexafluoropropylene, polyvinylidine fluoride, polyvinylfluoride, copolymer mixtures of tetrafluoroethylene and ethylene, and mixtures of tetrafluoroethylene, propylene and flourinated copolymers of ethylene propylene.

In addition to the above identified ingredients, the composition of the invention may also include flavors (artificial or natural) and colorants.

In order to prepare the composition of the invention, the evaporation promoting compound, polyurethane resin and poly(fluoro) compound are dissolved in the solvent until the system is homogenous. Heat may be applied to facilitate dissolution.

For application to dentures, the composition should include a solvent in an amount between about 66 and 98 weight percent, an evaporation promoting compound such as N-methylpyrrolidinone in an amount between about 0.5 and 15 weight percent, a polyurethane resin in an amount between about 1 and 25 weight percent and a poly(fluoro) compound such as polytetra-fluorethylene (Teflon) in an amount between about 0.5 and 20 weight percent.

Preferably, the solvent is present in an amount between about 75 and 97 weight percent. The preferred evaporation promoting compound is N-methylpyrrolidinone in an amount between about 1 and 8 weight percent.

If the solvent is either water or an alcohol, as stated hereinabove, a water based aliphatic polyurethane resin is chosen and is present in an amount between about 2 and 15 weight percent. If instead a ketone is used as a solvent, a non-water based aromatic resin is chosen and is present in an amount between about 2 and 20 weight percent.

Polytetra-fluoroethylene is the preferred hydrocarbon and is present in an amount between about 0.5 and 3 weight percent.

In order to better comprehend the composition of the invention as applied to dentures and other artificial teeth, the following preferred examples are provided.

EXAMPLE 1

| | |
|---|---|
| Water | 96 weight percent |
| | (96 grams) |
| N-methyl-pyrrolidinone | 1 weight percent |
| | (1 gram) |
| Polyurethane | 2.4 weight percent |
| | (2.4 grams) |
| Polytetra-fluorethylene | 0.6 weight percent |
| | (0.6 grams) |

EXAMPLE 2

| | |
|---|---|
| Ethanol | 96 weight percent |
| | (96 grams) |
| N-methylpyrrolidinone | 1 weight percent |
| | (1 gram) |
| Polyurethane | 2.4 weight percent |
| | (2.4 grams) |
| Polytetra-fluorethylene | 0.6 weight percent |
| | (0.6 grams) |

In order to test the effectiveness of the preferred water based (Example 1) denture composition, the following experiment was conducted.

Ten acrylic disks (diameter 23mm, thickness 4mm) were coated on one side with the denture composition and allowed to dry for two hours (the other side was left the same and uncoated). The disks were then placed in a 2% solution of Methylene Blue (Basic Blue 9, C.I. 52015)(made up of 2 grams of Methylene Blue with 98 grams of water) in a 400 mL beaker and stirred for two hours.

After two hours, the disks were then removed from the methylene blue solution, rinsed with water and air dried. In all cases, the disk sides that were not coated with the denture solution were stained with the methylene blue. Removal of the methylene blue stain was not possible even by rubbing the disks with a paper towel (the blue stain was permanently fixed on the acrylic disk). The other sides of the disks with the denture coating of the invention remained unstained, thus demonstrating the effectiveness of the inventive denture composition.

In examples 1 and 2, the polyurethane resin is a water based aliphatic polyurethane with an acid group functionality.

The following are further examples of the denture composition of the invention:

EXAMPLE 3

| | |
|---|---|
| Acetone | 70% (70 grams) |
| 5-methyl-2-pyrrolidinone | 5% (5 grams) |
| Polychlorotrifluorethylene | 15% (15 grams) |
| 2,4 TDI/ED/PPO | 10% (10 grams) |

EXAMPLE 4

| | |
|---|---|
| Isopropylalcohol | 80% (80 grams) |
| 1-ethyl-2-pyrrolidinone | 12% (12 grams) |
| Polyvinylidine fluoride | 5% (5 grams) |
| MDI/EG/PPO | 3% (3 grams) |

EXAMPLE 5

| | |
|---|---|
| Isopropylacetone | 85% (85 grams) |
| 2-Pyrrolidone | 3% (3 grams) |
| Polyvinylfluoride | 9% (9 grams) |
| MDI/ED/PEO | 3% (3 grams) |

In order to use the composition of the invention on dentures, the dentures are first removed and then cleaned and dried. Thereafter, the composition is preferably sprayed on all external surfaces of the denture by means of a pump or aerosol delivery device. Spraying should take place evenly for between approximately 2 and 7 seconds.

After spraying, the dentures are air dried for at least one hour, and preferably for about two hours. From a practical standpoint, the spraying of the dentures with the dental composition should take place prior to the denture wearer going to bed so that the dentures are sufficiently dry after the spraying process is completed. If that is not convenient, then the sprayed dentures may be rapidly dried by using a hair dryer or other similar drying or air source.

For most denture wearers, application of the composition to one's dentures is required only once a week. If the composition of the invention is properly applied, the accumulation of plaque and other debris along the dentures+ surfaces is substantially prevented. As a result, routine cleaning of the treated dentures is quicker and more efficient.

Moreover, it has been found that the composition of the invention helps maintain retention of the dentures in the wearer's mouth. Furthermore, use of the denture composition reduces mouth odors of the denture wearer.

Although the composition of the invention has been described as being suitable for spraying onto a denture material, the composition may be applied to dentures or other artificial teeth in other ways, such as dipping or painting.

For application to a dental implant, the composition is more concentrated than the composition preferred for application to dentures, and preferably includes a solvent in an amount between about 46 and 76 weight percent, a volatile compound such an N-methylpyrrolidinone in an amount between about 5 and 25 weight percent, a polyurethane resin in an amount between about 10 and 35 weight percent and a poly(fluoro) compound such as polytetra-fluorethylene (Teflon) in an amount between about 5 and 20 weight percent.

Preferably, the solvent is present in an amount between about 50 and 66 weight percent. The preferred evaporation promoting compound is N-methylpyrrolidinone in an amount between about 9 and 20 weight percent.

If the solvent is either water or an alcohol, as stated hereinabove, a water based aliphatic polyurethane resin is chosen and is present in an amount between about 5 and 25 weight percent. If instead a ketone is used as a solvent, a non-water based aromatic resin is chosen and is present in an amount between about 5 and 25 weight percent.

Polytetra-fluoroethylene is the preferred hydrocarbon and is present in an amount between about 5 and 15 weight percent.

In order to better understand the composition of the invention as applied to a dental implant, the following preferred examples are provided:

EXAMPLE 1

| | |
|---|---|
| Water | 66 weight percent |
| | (66 grams) |
| N-Methylpyrrolidinone | 9 weight percent |
| | (9 grams) |
| Polyurethane | 20 weight percent |
| | (20 grams) |
| Polytetra-fluorethylene | 5 weight percent |
| | (5 grams) |

EXAMPLE 2

| | |
|---|---|
| Water | 64 weight percent |
| | (64 grams) |
| Ethanol | 2 weight percent |
| | (2 grams) |
| N-Methylpyrrolidinone | 9 weight percent |
| | (9 grams) |
| Polytetra-fluorethylene | 5 weight percent |
| | (5 grams) |
| Polyurethane | 20 weight percent |

EXAMPLE 3

| Acetone | 70 weight percent |
| --- | --- |
|  | (70 grams) |
| 5-methyl-2-pyrrolidinone | 5 weight percent |
|  | (5 grams) |
| Polychlorotrifluorethylene | 15 weight percent |
|  | (15 grams) |
| 2,4 TDI/ED/PPO | 10 weight percent |
|  | (10 grams) |

EXAMPLE 4

| Isopropylalcohol | 60 weight percent |
| --- | --- |
|  | (60 grams) |
| 1-ethyl-2-pyrrolidinone | 12 weight percent |
|  | (12 grams) |
| Polyvinylidine fluoride | 15 weight percent |
|  | (15 grams) |
| MDI/EG/PPO | 13 weight percent |
|  | (13 grams) |

EXAMPLE 5

| Isopropylacetone | 55 weight percent |
| --- | --- |
|  | (55 grams) |
| 2-Pyrrolidone | 13 weight percent |
|  | (13 grams) |
| Polyvinylfluoride | 9 weight percent |
|  | (9 grams) |
| MDI/ED/PEO | 23 weight percent |
|  | (23 grams) |

EXAMPLE 6

| 1-pentanol | 68 weight percent |
| --- | --- |
|  | (68 grams) |
| Diethylether | 12 weight percent |
|  | (12 grams) |
| Polyvinylidine fluoride | 10 weight percent |
|  | (10 grams) |
| NDI/ED/PEO | 5 weight percent |
|  | (5 grams) |

In order to use the composition of the invention on a dental implant, the implant neck is removed (by the dentist) and then cleaned and dried. Thereafter, the neck of the implant is soaked in the inventive composition for about 10-30 seconds. After dipping, the implant neck is air dried for at least two hours.

Alternatively, the inventive composition may be applied to the implant neck by painting.

For most implants, application of the more concentrated form of the inventive composition should be about once every three months. If the composition is properly applied, the accumulation of plaque and other debris along the neck of the implant is substantially prevented. Moreover, there would no longer be the need to scrape and thereby possibly damage the implant surface.

It will thus be seen that the objects set forth above, and those made apparent from the preceding description, are efficiently attained, and since certain changes may be made in carrying out the above method and in the composition set forth above without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method for preventing the build-up of plaque and other debris on artificial teeth or a dental implant comprising applying a composition to the artificial teeth or dental implant containing a solvent selected from the group consisting of water, ethanol, methanol, isopropyl alcohol, 3-pentanol, 1-pentanol, 1-hexanol, 2-hexanol, 3-hexanol, isobutyl alcohol, methylethyl ketone, acetone, allylacetone, isopropyl acetone, methylpropyl ketone, 3-pentanone, 3-hexanone and 2-hexanone, an evaporation promoting compound selected from the group consisting of N-methylpyrrolidinone, 2-pyrrolidone, 2-pyrrolidoneacetamide, 1-ethyl-2-pyrrolidinone and 5-methyl-2-pyrrolidinone, diethylether, isopropylether and pentylether in an amount between about 0.5 and 25 weight percent, at least one adduct of a diisocyanate selected from the group consisting of 1,6-hexane diisocyanate, isophorone diisocyanate, 2,4-toluene diisocyanate, 2,6-toluene diisocyanate, methylene bis (p-phenylisocyanate) and 1,5-naphthalene diisocyanate and a polyol selected from the group consisting of polyethylene oxide, polypropylene oxide, polyisobutylene and polytetramethylene oxide in an amount between about 1 and 35 weight percent, and a polyfluorinated hydrocarbon selected from the group consisting of polytetrafluoroethylene, polychlorotrifluoroethylene, polyhexafluoropropylene, polyvinylidine fluoride, polyvinyl fluoride, copolymer mixtures of tetrafluoroethylene and ethylene, and mixtures of tetrafluoroethylene, propylene and fluorinated copolymers of ethylene propylene in an amount between about 0.5 and 20 weight percent.

2. The method of claim 1, wherein the solvent is selected from the group consisting of ethanol and methylethyl ketone in an amount between about 50 and 97 weight percent.

3. The method of claim 1, wherein the evaporation promoting compound is N-methylpyrrolidinone in an amount between about 1 and 20 weight percent.

4. The method of claim 1, wherein the solvent is water or an alcohol and the adduct is water-based.

5. The method of claim 1, wherein the solvent is a ketone and the adduct is not water based.

6. The method of claim 1, wherein the polyfluorinated hydrocarbon is polytetrafluoroethylene in an amount between about 0.5 and 15 weight percent.

7. A method for preventing the build-up of plaque and other debris on artificial teeth or a dental implant comprising applying a composition to the artificial teeth or dental implant containing a solvent selected from the group consisting of water, ethanol, methanol, isopropyl alcohol, 3-pentanol, 1-pentanol, 1-hexanol, 2-hexanol, 3-hexanol, isobutyl alcohol, methylethyl ketone, acetone, allylacetone, isopropyl acetone, methylpropyl ketone, 3-pentanone, 3-hexanone and 2-hexanone, an evaporation promoting compound selected from the group consisting of N-methylpyrrolidinone, 2-pyrrolidone, 2-pyrrolidoneacetamide, 1-ethyl-2-pyrrolidinone and 5-methyl-2-pyrrolidinone, diethylether, isopropylether and pentylether in an amount between about 0.5 and 25 weight percent, at least one adduct of a diisocyanate and a polyol in an amount between about 1 and 35 weight percent, and a polyfluorinated hydrocarbon in an amount between about 0.5 and 20 weight percent.

8. The method of claim 7, wherein the solvent is ethanol in an amount between about 50 and 97 weight percent.

9. The method of claim 7, wherein the solvent is methylethyl ketone in an amount between about 50 and 97 weight percent.

10. The method of claim 7, wherein the evaporation promoting compound is N-methylpyrrolidinone in an amount between about 1 and 20 weight percent.

11. The method of claim 7, wherein said at least one adduct of a diisocyanate and a polyol is selected from the group consisting of water based aliphatic adducts of diisocyanates and polyols and non-water based aromatic adducts of diisocyanates and polyols.

12. The method of claim 11, wherein the solvent is selected from the group consisting of water, ethanol, methanol, isopropyl alcohol, 3-pentanol, 1-pentanol, 1-hexanol, 2-hexanol, 3-hexanol, and isobutyl alcohol and wherein the adduct is water based.

13. The method of claim 11, wherein the solvent is selected from the group consisting of methylethyl ketone, acetone, allyl-acetone, isopropyl acetone, methylpropyl ketone, 3-pentanone, 3-hexanone and 2-hexanone and wherein the adduct is not water based.

14. The method of claim 7, wherein the polyfluorinated hydrocarbon is selected from the group consisting of polytetrafluoroethylene, polychlorotrifluoroethylene, polyhexafluoropropylene, polyvinylidine fluoride, copolymer mixtures of tetrafluoroethylene and ethylene, and mixtures of tetrafluoroethylene, propylene and fluorinated copolymers of ethylene propylene.

15. The method of claim 14, wherein the fluorinated hydrocarbon is polytetrafluorethylene in an amount between about 0.5 and 15 weight percent.

16. The method of claim 7, wherein the evaporation promoting compound is N-methylpyrrolidinone and the polyfluorinated hydrocarbon is polytetrafluorethylene.

17. The method of claim 7, wherein said applying step for artificial teeth comprises spraying the artificial teeth with said composition.

18. The method of claim 7, wherein said applying step for said dental implant comprises soaking the implant in said composition.

19. The method of claim 7, wherein said applying step for said dental implant comprises painting the implant with said composition.

20. The method of claim 7, further including the step of cleaning the artificial teeth or dental implant prior to said applying step.

21. The method of claim 20, further including the step of drying the artificial teeth or dental implant prior to said applying step.

22. The method of claim 7, further including the step of drying the artificial teeth or dental implant after said applying step.

23. The method of claim 22, wherein said drying step comprises air drying the artificial teeth or dental implant for between one and two hours.

24. The method of claim 22, wherein said drying step comprises drying the artificial teeth or dental implant using a heat or air source.

25. The method of claim 17, wherein said spraying step occurs about once a week.

26. The method of claim 18, wherein said soaking step occurs about once every three months.

* * * * *